United States Patent [19]

Ponomarev et al.

[11] 4,031,119
[45] June 21, 1977

[54] [PERFLUOROALKYL(ALKOXY)PHENYL]-METHYLDICHLOROSILANES AND METHOD OF PREPARING SAME

[76] Inventors: Alexei Ivanovich Ponomarev, prospekt Stachek, 59, korpus 2, kv. 47; Sergei Vasilievich Sokolov, ulitsa III Internatsionala, 67, kv. 222; Julia Alexeevna Larionova, prospekt Elizarova, 12, kv. 15; Alexandr Leibovich Klebansky, ulitsa Zhelyabova, 10, kv. 107, all of Leningrad; Vsevolod Volfovich Berenblit, Vsevolozhsky raion, poselok Kuzmolovsky, ulitsa Nagornaya, 23, kv. 10; Jury Pavlovich Dolnakov, Krasnoe selo, ulitsa Narvskaya, 4, kv. 122, both of Leningradskaya oblast; Lev Moiseevich Yagupolsky, ulitsa Ivana Kudri, 41, kv. 48, Kiev; Vladlen Vasilievich Malovik, ulitsa Osipovskogo, 4/5, kv. 6, Kiev; Miron Onufrievich Lozinsky, ulitsa Voroshilova, 18, kv. 13, Kiev; Viktor Mikhailovich Belous, ulitsa Ujutnaya, 5a, kv. 3, Odessa; Boris Efimovich Gruz, ulitsa Kurskaya, 10, kv. 18, Kiev; Ljubov Antonovna Alexeeva, Proletarsky bulvar, 41, kv. 28, Odessa; Anatoly Kirillovich Ankudinov, ulitsa Lensoveta, 10, kv. 203; Rufina Mikhailovna Ryazanova, Vitebsky prospekt, 81, korpus 1, kv. 6, both of Leningrad, all of U.S.S.R.

[22] Filed: Apr. 29, 1976

[21] Appl. No.: 681,521

[52] U.S. Cl. ..................... 260/448.2 B
[51] Int. Cl.² ..................... C07F 7/12
[58] Field of Search ............ 260/448.2 B, 448.2 R

[56] References Cited

UNITED STATES PATENTS

| | | | |
|---|---|---|---|
| 3,422,131 | 1/1969 | Pittman et al. | 260/448.2 B |
| 3,450,738 | 6/1969 | Blochl | 260/448.2 B X |
| 3,484,470 | 12/1969 | Pittman et al. | 260/448.2 B |

OTHER PUBLICATIONS

Bazant et al., "Organosilicon Compounds", vol. 2, Part 1, Academic Press, N.Y. (1965), p. 254.

Primary Examiner—Paul F. Shaver

[57] ABSTRACT

The invention relates to [perfluoroalkyl(alkoxy)-phenyl]methyldichlorosilanes characterized by the general formula

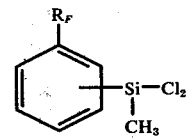

(I), where: $R_F$ = $OCF_3$, $OC_2F_5$, $OC_2F_4OCF_3$, $C_2F_4OCF_3$, $C_3F_7$ and also to a method of preparing them.

The method according to the invention consists in that fluorobromo[alkyl(alkoxy)]benzenes having the general formula

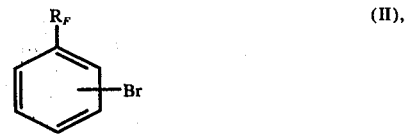

(II), where: $R_F$ = $OCF_3$, $OC_2F_5$, $OC_2F_4OCF_3$, $C_2F_4OCF_3$, $C_3F_7$ are treated with magnesium taken in a 5 - 20 per cent excess with respect to the stoichiometric quantity in a solution of absolute diethyl ether or absolute tetrahydrofurane at a temperature of 8° - 60° C. The resulting fluorine-containing magnesiumbromo[alkyl(alkoxy)]benzenes are treated with three-functional silanes — methyltrichlorosilane — taken in a 100 - 500 per cent excess with respect to the stoichiometric quantity, or with methylchlorodiethoxysilane, taken in the stoichiometric quantity or in a 50 per cent excess with respect to the stoichiometric quantity, at a temperature of 18° - 60° C. In the case of methylchlorodiethoxysilane, the resultant product is fluorine-containing [alkyl(alkoxy)phenyl]methyldiethoxysilanes which are treated with acetyl chloride taken in a 25 - 50 per cent excess with respect to the stoichiometric quantity, at a temperature of 40° - 70° C, in the presence of ferric chloride as a catalyst.

The proposed [perfluoroalkyl(alkoxy)phenyl]methyldichlorosilanes can be used for preparing organofluosilicon lubricants, greases, sealing counds, rubber mixtures having high resistance to heat, frost, petrol and oils, that can be used in various fields of technology.

The described method can be used to obtain the proposed end products in yields as high as 96 per cent of theory.

4 Claims, No Drawings

[PERFLUOROALKYL(ALKOXY)PHENYL]METHYLDICHLOROSILANES AND METHOD OF PREPARING SAME

The present invention relates to novel compounds, [perfluoroalkyl(alkoxy)phenyl]methyldichlorosilanes, and to a method of preparing them.

[Perfluoroalkyl(alkoxy)phenyl]methyldichlorosilanes, according to the invention, are compounds characterized by the following general formula

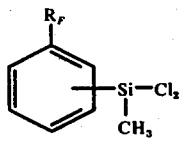

(I), where: $R_F$ = $OCF_3$, $OC_2F_5$, $OC_2F_4OCF_3$, $C_2F_4OCF_3$, $C_3F_7$

Said compounds can be used for preparing organofluosilicon lubricants greases, sealing compounds and rubber mixtures, having high thermal stability (to 370°–415° C), frost-resistance (glass-transition temperature −71° to −65° C), benzine-and oil-resistance. Said oils, lubricants, sealing compounds and rubbers mixtures are insoluble in benzine, hexane, benzene, toluene, or other non-polar solvents; they are insoluble in mineral oils either. Said organofluosilicon lubricants, greases, sealing compounds and rubber mixtures can be used in various fields of technology, for example, in instrument-making, automobile, aircraft, and other industries.

Moreover, the proposed [perfluoroalkyl(alkoxy)phenyl]methyldichlorosilanes can be used for preparing anti-foaming agents that are used as additives to mineral oils.

The proposed [perfluoroalkyl(alkoxy)phenyl]methyldichlorosilanes can be produced by the method according to the invention consisting in that fluorine-containing bromo [alkyl(alkoxy)] benzenes having the general formula

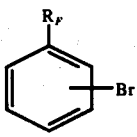

(II), where: $R_F$ = $OCF_3$, $OC_2F_5$, $OC_2F_4OCF_3$, $C_2F_4OCF_3$, $C_3F_7$ are treated with magnesium taken in a 5 – 20 percent excess with respect to the stoichiometric quantity, in a solution of absolute diethyl ether or absolute tetrahydrofurane, at a temperature of 8° – 60° C, with subsequent treatment of the resulting fluorine-containing magnesium-bromo [alkyl(alkoxy)]-benzenes with three-functional silanes — methyltrichlorosilane — taken in a 100 – 500 percent excess with respect to the stoichiometric quantity, or with methylchlorodiethylethoxysilane taken in the stoichiometric quantity or in a 50 percent excess with respect to stoichiometric quantity, at a temperature of 18° -60° C; in the case of methylchlorodiethoxysilane, the resultant products are fluorine-containing [alkyl(alkoxy)phenyl]methyldiethoxysilanes that are further treated with acetyl chloride, taken in a 25 – 50 percent excess with respect to the stoichiometric quantity, at a temperature of 40° – 70° C, in the presence of ferric chloride as a catalyst.

This method can be effected under mild conditions; the yield of products attained with the proposed method is high, viz., to 96 percent of theory.

To accelerate the reaction between fluorine-containing bromo[alkyl(alkoxy)]benzenes and magnesium, it is recommendable that the process should be carried out in the presence of methyl iodide.

To ensure better separation of magnesium salts that are produced by treating fluorine-containing magnesiumbromo[alkyl(alkoxy)]benzenes with three-functional silanes, it is recommendable that the process should be carried out in the presence of absolute hexane taken in the quantity of 30 – 400 percent of the weight of the three-functional silane.

For a better understanding of the invention, the following examples of its practical embodiment are given by way of illustration.

EXAMPLE 1

Preparation of (meta-trifluoromethoxyphenyl)methyldichlorosilane from meta-bromo(trifluoromethoxy)benzene.

First, meta-bromo(trifluoromethoxy)benzene is prepared by heating 4.4 g (0.02 mole) of meta-bromophenol fluoformate, 5 g of hydrogen fluoride, and 4 g of sulphur tetrafluoride in a 70-ml stainless steel autoclave at a temperature of 100° C for two hours. The autoclave is then cooled and gas is released out of it. The reaction products are distilled with steam. The distillate is extracted with ethyl ether. The ethereal solution is washed with water, a 10 percent of sodium hydroxide solution then once more with water, and dried over sodium sulphate. Diethyl ether is removed by distillation and the residue is distilled in vacuum. The yield of meta-bromo(trifluoromethoxy)benzene is 3.62 g (77.8 percent of theory).

The boiling point is 78° – 81° C (at 55 mm Hg)
$d_4^{25}$ = 1.635; $n_D^{25}$ = 1.4592

Found: $MR_D$ = 39.97. $C_7H_4OBrF_3$ Calculated: $MR_D$ = 40.30

The above-named end product, (meta-trifluoromethoxyphenyl)methyldichlorosilane is synthesized as follows.

A three-neck flask is filled with 27.6 g of (1.03 g-atom + 10 percent excess with respect to the stoichiometric quantity) of magnesium in 750 ml of absolute diethyl ether and then ten drops of meta-bromo(trifluoromethoxy)benzene are added at a temperature of 36° C (ether boiling point). As soon as the solution becomes turbid the temperature in the flask is lowered to 10° – 12° C and a solution of meta-bromo(trifluoromethoxy)benzene in absolute diethyl ether is added with intensive stirring within eight hours. The total quantity of meta-bromo(trifluoromethoxy)benzene added is 248.05 g (1.03 mole) in 250 ml of absolute diethyl ether. The reaction mixture is heated to a temperature of 36° C and kept at this temperature for two hours. The resultant product is a solution of meta-magnesium-bromo(trifluoromethoxy)benzene in diethyl ether.

A three-neck flask is loaded with 216.9 g (1.28 mole, i.e. a 25 percent excess of stoichiometric quantity) of methylchlorodiethoxysilane and the solution of meta-magnesium-bromo(trifluoromethoxy)benzene in diethyl ether is added from a dropping funnel at a temperature of 18° – 20° C. The temperature of the reaction mixture rises to 35° C. As soon as the said solution is all added into the flask, the reaction mixture is heated to 40° C and kept at this temperature with intensive stirring (to complete the reaction) for eight hours. The solution is then passed through a Shott filter to separate from magnesium salts, whereupon diethyl ether and excess methylchlorodiethoxysilane are removed from the solution by distillation. As the residue is rectified on a column (ten theoretical plates), 211.9 g (70 percent of theory) of (metatrifluoromethoxyphenyl)methyldiethoxysilane are obtained.

The boiling point is 114° – 114.5° C (at 20 mm Hg) $d_4^{20} = 1.148$; $n_D^{20}$ 9 1.4365

Found: $MR_D = 67.0$ $C_{12}H_{17}SiO_3F_3$ Calculated: $MR_D = 67.37$ Elemental analysis Found, in percent: C, 48.45; H, 5.72; Si, 9.32; F, 19.60. $C_{12}H_{17}SiO_3F_3$; Calculated, in percent: C, 48.96; H, 5.85; Si, 9.50; F, 19.40.

A three-neck flask is loaded with 318.1 g (1.08 mole) of (meta-trifluoromethoxyphenyl)methyldiethoxysilane and 0.01 g of ferric chloride. From a dropping funnel added are 212 g (2.7 mole i.e., 25 percent excess of stoichiometric quantity) of acetyl chloride at such a rate that the temperature does not rise above 40° C. As the whole required amount is added, the reaction mixture is heated to a temperature of 70° C and kept at this temperature for two hours. As a result of the rectification process on a column (ten theoretical plates) the yield of (meta-trifluoromethoxyphenyl)methyldichlorosilane is 290.6 g (97.7 percent of theory).

The boiling point is 81.2° C (at 10 mm Hg) $d_4^{20} = 1.344$; $n_D^{20} = 1.4560$ Found: $MR_D = 55.63$ $C_8H_7SiOF_3Cl_2$ Calculated: $MD = 55.81$ Elemental analysis Found, in percent: C, 34.75; H, 2.40; Si, 9.95; F, 20.35; Cl, 25.61; $C_8H_7SiOF_3Cl_2$ Calculated, C, percent: c, 34.89; H, 2.59; Si, 10.18; F, 20.72; Cl, 25.78.

EXAMPLE 2

Preparation of (para-trifluoromethoxyphenyl)-methyldichlorosilane from para-bromo(trifluoromethoxy)benzene.

First para-bromo(trifluoromethoxy)benzene is prepared as follows. 4.6 g (0.02 mole) of para-bromophenol fluoformate, 5 g of hydrogen fluoride, and 4 g of sulphur tetrafluoride are heated in a 70-ml stainless steel autoclave at a temperature of 100° C for two hours. The autoclave is then cooled and gas is released out of it. The reaction products are distilled with steam and the distillate is extracted with diethyl ether. The ethereal solution is washed with water, 10 percent solution of sodium hydroxide, then with water, and dried over sodium sulphate. Diethyl ether is removed by distillation and the residue is distilled in vacuum. The yield of para-bromo(trifluoromethoxy)benzene is 4.03 g (72 percent of theory).

The boiling point is 80° – 82° C (at 50 mm Hg) $n_D^{25} = 1.4587$

The above-named end product — (para-trifluoromethoxyphenyl)methyldichlorosilane is synthesized as follows.

A three-neck flask is filled with 13.8 g (0.51 g-atom + 10 percent excess of stoichiometric quantity) of magnesium in 370 ml of absolute diethyl ether, and then 5 drops of para-bromo(trifluoromethoxy)benzene are added to it at the ether boiling point (36° C). As soon as the solution becomes turbid, the temperature inside the flask is lowered to 120° C and para-bromo(trifluoromethoxy)benzene in absolute diethyl ether is added at this temperature with intensive stirring of the reaction mixture within four hours. The total amount of para-bromo(trifluoromethoxy)benzene added into the flask is 12.3 g (0.51 mole) in 150 ml of absolute diethyl ether. The reaction mixture is then heated to a temperature of 36° C and kept at this temperature for an hour to obtain a solution of para-magnesiumbromo(trifluoromethoxy)benzene in absolute diethyl ether.

A three-neck flask is filled with 305.2 g (2.04 mole, i.e. a 300 percent excess with respect to the stoichiometric quantity) of methyltrichlorosilane and the solution of para-magnesiumbromo(trifluoromethoxy)benzene in absolute diethyl ether is added from a dropping funnel at a temperature of 18° – 20° C. The temperature of the reaction mixture rises to 30° C in this process. As soon as the whole required quantity of said solution has been added, the reaction mixture is heated to a temperature of 40° C and kept at this temperature for 5 hours with intensive stirring to complete the reaction. The solution is then filtered to separate magnesium salts, and diethyl ether and excess methyltrichlorosilane are removed from the obtained filtrate by distillation. The residue is rectified on a column (10 theoretical plates) to isolate (para-trifluoromethoxyphenyl)methyldichlorosilane. The yield of the product is 108.5 g, which is 79.2 percent of theory.

The boiling point is 81.8° C at 10 mm Hg $d_4^{20} = 1.348$; $n_D^{20} = 1.4565$ Found: $MR_D = 55.65$. $C_8H_7SiOF_3Cl_2$ Calculated: $MR_D = 55.81$ Elemental analysis Found, in percent: C, 34.65; H, 2.45; Si, 10.10; F, 20.54; Cl, 25.82. $C_8H_7SiOF_3Cl_2$ Calculated, in percent: C, 34.89; H, 2.59; Si, 10.18; F, 20.72; Cl, 25.78

EXAMPLE 3

Preparation of ortho-trifluoromethoxyphenyl)methyldichlorosilane from ortho-bromo(trifluoromethoxy)benzene.

First, ortho-bromo(trifluoromethoxy)benzene is prepared as follows. 4.3 g (0.02 mole) of ortho-bromophenol fluoformate, 5g of hydrogen fluoride, and 4.5 g of sulphur tetrafluoride are heated in a 70-ml stainless steel autoclave at a temperature of 100° C for two hours. The autoclave is then cooled and gas is released out of it. The reaction products are distilled with steam, and the distillate is extracted with diethyl ether. The ethereal solution is washed with water, 10 percent sodium hydroxide solution again with water, and then dried over sodium sulphate. Diethyl ether is removed by distillation, and the residue is distilled in vacuum. The yield of ortho-bromo(trifluoromethoxy)benzene is 3.25 g (72 percent of theory).

The boiling point is 80° –81° C (at 50 mm Hg). $n_D^{25} = 1.4598$

The above-named end product — (ortho-trifluoromethoxyphenyl)methyldichlorosilane is synthesized as follows.

A three-neck flask is filled with 6.9 g (0.25 g-atom + a 10 percent excess with respect to the stoichiometric quantity) of magnesium in 200 ml of absolute diethyl ether, and, at a temperature of 36° C (boiling point of the ether), ten drops of ortho-bromo(trifluoromethoxy)benzene, and 5 drops of methyl iodide are added. As soon as the solution becomes turbid, the temperature in the flask is lowered to 10° C, and the solution of ortho-bromo(trifluoromethoxy)benzene in absolute diethyl ether is added at this temperature with intensive stirring within three hours. The total quantity of ortho-bromo(trifluoromethoxy)benzene added into the flask is 62 g (0.25 mole) in 70 ml of absolute diethyl ether. The reaction mixture is then heated to 36° C and kept at this temperature for an hour. The resultant product is a solution of ortho-megnesiumbromo(trifluoromethoxy)benzene in absolute diethyl ether.

A three-neck flask is charged with 112.2 g (0.75 mole, i.e. a 200 percent excess with respect to the stoichiometric quantity) of methyltrichlorosilane in 300 ml of absolute hexane and then the solution of ortho-magnesiumbromo(trifluoromethoxy)benzene in absolute diethyl ether is added from a dropping funnel at a temperature of 18° – 20° C. The temperature in the reaction zone rises to 30° C, and as soon as the whole quantity of the solution has been added, the reaction mixture is heated to 40° C and kept at this temperataure with intensive stirring for three hours to complete the reaction. The solution is then filtered to separate from magnesium salts, and the solvents (diethyl ether and hexane) are distilled off together with excess methyl trichlorosilane. The residue is rectified on a 10-plane column to isolate 44.7 g (65 percent of theory) of (ortho-trifluoromethoxyphenyl)methyldichlorosilane.

The boiling point is 80° – 81° C (at 10 mm Hg) $d_4^{20}$ = 1.350; $n_D^{20}$ 1.4556

Found: $MR_D$ = 55.71. $C_8H_7SiOF_3Cl_2$ Calculated: $MR_D$ = 55.81 Elemental analysis Found, in percent: C, 34.76; H, 2.38; Si, 10.25; F, 20.42; Cl, 26.02 $C_8H_7SiOF_3Cl_2$; Calculated, in percent: C, 34.89; H, 2.59; Si, 10.18; F, 20.72; Cl, 25.78.

EXAMPLE 4

Preparation of (meta-pentafluoroethoxyphenyl)methyldichlorosilane from meta-bromo(pentafluoroethoxy)benzene.

First meta-bromo(pentafluoroethoxy)benzene is prepared by the following procedure. A 70-ml stainless steel autoclave is charged with 5.38 g (0.02 mole) of meta-bromophenol trifluoroacetate, 7 g of hydrogen fluoride, and 4 g of sulphur tetrafluoride and the contents are heated at a temperature of 100° C for two hours. The autoclave is then cooled and gas is released out of it. The reaction products are distilled with steam. The distillate is extracted with diethyl ether. The ethereal solution is washed with water, 10 percent solution of sodium hydroxide, again with water, and then dried over sodium sulphate. Diethyl ether is removed by distillation and the residue is distilled in vacuum. The yield of meta-bromo(pentafluoroethoxy)benzene is 4.37 g (75.4 percent of theory).

The boiling point is 77° – 79° C (at 30 mm Hg). $d_4^{25}$ = 1.665; $n_D^{25}$ = 1.4285

Found: $MR_D$ = 45.61. Calculated: $MR_D$ = 45.96 Elemental analysis Found, in percent: Br, 27.59, 27.68; F, 32.51, 32,50 $C_8H_4OBrF_5$ Calculated, in percent: Br, 27.47; F, 32.66

The end-product — (meta-phentafluoroethoxyphenyl)methyldichlorosilane is synthesized as follows.

A three-neck flask is charged with 10.07 g (0.377 g-atom + a 10 percent excess with respect to the stoichiometric quantity) of magnesium in 340 ml of absolute diethyl ether, and then five drops of meta-bromo(pentafluoroethoxy)benzene are added at a temperature of 36° C (boiling point of the ether). Finally two drops of methyl iodide are added and as soon as the solution in the flask becomes turbid, the temperature in the flask is lowered to 7° – 8° C and the solution of meta-bromo(pentafluoroethoxy)benzene in absolute diethyl ether is added during four hours with intensive stirring at the same temperature of 7° – 8° C. The total quantity of meta-bromo(pentafluoroethoxy)benzene added is 109.9 g (0.377 mole) in 100 ml of absolute diethyl ether. The reaction mixture is then heated to a temperature of 36° C and kept at this temperature for an hour. The resultant product is a solution of meta-magnesiumbromo(pentafluoroethoxy)benzene in diethyl ether.

A three-neck flask is charged with 63.53 g (0.377 mole, i.e. the stoichiometric quantity) of methylchlorodiethoxysilane in 400 ml of absolute hexane and then the solution of meta-magnesiumbromo(pentafluoroethoxy)benzene in diethyl ether is added from a dropping funnel at a temperature of 18° – 20° C. The temperature in the reaction mixture rises to 30 °C, and as the whole quantity of the solution has been added, the temperature is raised to 36° – 40° C and the reaction mixture is kept at this temperature for three hours with intensive stirring to complete the reaction. The solution is then passed through a Shott filter to separate from magnesium salts, and then the solvents (diethyl ether and hexane) are removed by distillation. After rectification on a column (ten theoretical plates), 98.0 g of (meta-pentafluoroethoxyphenyl)methyldiethylethoxysilane are isolated, which makes 73.1 percent of theory.

The boiling point is 104.5° – 105° C at 8 mm Hg $d_4^{20}$ = 1.177; $n_D^{20}$ = 1.4119

Found: $MR_D$ = 72.68. $C_{13}H_{17}SiO_3F_5$ Calculated: $MR_D$= 72.06 Elemental analysis Found, in percent: C, 45.62; H, 5.19; Si, 8.31; F, 28.00 $C_{13}H_{17}SiO_3F_5$ Calculated, in percent: C 45.32; H, 4.97; Si, 8.16; F, 27.58

A three-neck flask is charged with 40.61 g (0.12 mole) of (meta-pentafluoroethoxyphenyl)methyldiethoxysilane and 0.005 g of ferric chloride. Next, 24 g (0.3 mole, i.e. a 25 percent excess with respect to the stoichiometric quantity) of acetyl chloride are added from a dropping funnel at a rate that would ensure the rise of temperature of the reaction mixture not above 40° C. As the whole required quantity has been added, the reaction mixture is heated to 70° C and kept at this temperature for two hours. The yield of the rectified product is 36.9 g, which makes 96.5 percent of theory.

The boiling point of (meta-pentafluoroethoxyphenyl)methyldichlorosilanes is 89.5° C (at 10 mm Hg) $d_4^{20}$ = 1.3881; $n_D^{20}$ = 1.4353

Found, $MR_D$ = 61.0. $C_9H_7SiOF_5Cl_2$ Calculated: $MR_D$ = 60.54 Elemental analysis Found, in percent: C, 33.45; H, 2.25; Si, 8.82; F, 29.41; Cl, 21.96. $C_9H_7SiOF_5Cl_2$ Calculated, in percent: C, 33.23; H, 2.15; Si, 8.61; F, 29.23; Cl, 21.84

EXAMPLE 5

Preparation of para-pentafluoroethoxyphenyl)methyldichlorosilane from para-bromo(pentafluoroethoxy)benzene.

First, para-bromo(pentafluoroethoxy)benzene is prepared as follows. A 100-ml stainless steel autoclave is charged with 29.9 g (0.1 mole) of para-bromofluoroacetoxybenzene, 21.6 g (0.2 mole) of sulphur tetrafluoride, and 2.5 g of hydrogen fluoride, and the contents are heated at a temperature of 100° C for two hours, at a temperature of 150° C for two hours, and at a temperature of 175° C for six hours. When the reaction is complete the product is isolated with diethyl ether, washed with a 5 percent aqueous solution of sodium hydroxide, and dried over sodium sulphate.

Diethyl ether is removed by distillation and the residue is distilled in vacuum. The yield of para-bromo(pentafluoroethoxy)benzene is 18.5 g (63.0 percent of theory).

The boiling point is 91°–93° C (at 500 mm Hg). $n_D^{25} = 1.4327$; $d_4^{25} = 1.6540$ Found: $MR_D = 45.60$, $C_8H_4OBrF_5$ Calculated: $MR_D = 45.96$ Elemental analysis Found, in percent: Br, 27.59, 27.68; F, 32.39, 32.40 $C_8H_4OBrF_5$ Calculated, in percent: Br, 27.47; F, 32.66.

The end product — (para-pentafluoroethoxyphenyl)methyldichlorosilane is synthesized as follows.

A three-neck flask is charged with 5.02 g (0.172 g-atom + a 20 percent excess with respect to the stoichiometric quantity) of magnesium in 172 ml of absolute tetrahydrofurane and then five drops of the para-bromo(pentafluoroethoxy)benzene are added at a temperature of 56° C (the boiling point of tetrahydrofurane), and finally two drops of methyl iodide are added. As soon as the solution becomes turbid, the temperature in the flask is lowered to 18° C and, at this temperature, a solution of para-bromo(pentafluoroethoxy)benzene in absolute tetrahydrofurane is added with intensive stirring of the mixture. The total quantity of para-bromo(pentafluoroethoxy)benzene added is 50 g (0.172 mole) in 50 ml of absolute tetrahydrofurane. The reaction mixture is then heated to 60° C and kept at this temperature for thirty minutes. The resultant product is para-magnesiumbromo(pentafluoroethoxy)benzene solution in tetrahydrofurane.

A three-neck flask is charged with 28.9 g (0.172 mole, i.e. the stoichiometric quantity) of methylchlorodiethoxysilane in 200 ml of absolute hexane and then, at a temperature of 18° – 20° C, the solution of para-magnesiumbromo(pentafluoroethoxy)benzene in tetrahydrofuran is added from a dropping funnel. The temperature in the reaction zone rises to 30° C. As the whole required quantity of the solution has been added, the reaction mixture is heated to 56° – 60° C and kept at this temperature with intensively stirring for three hours to complete the reaction. The solution is then filtered to separate from magnesium salts, and the solvents tetrahydrofurane and hexane) are removed by distillation. The residue is rectified on a column (ten theoretical plates) to isolate 40.5 g (69 percent of theory) of (para-pentafluoroethoxyphenyl)methyldiethoxysilane.

The boiling point is 83.5° C (at 3 mm Hg) $d_4^{20} = 1.1972$; $n_D^{20} = 1.4170$ Found: $MR_D = 72.25$, $C_{13}H_{17}SiO_3F_5$ Calculated: $MR_D = 72.05$ Elemental analysis Found, in percent: H, 5.19, 4.77; F, 27.1, 27.4 $C_{13}H_{17}SiO_3F_5$ Calculated, in percent: H, 4.94; F, 27.61.

A three-neck flask is charged with 23.86 g (0.069 mole) of (para-pentafluoroethoxyphenyl)methyldiethoxysilane and 0.007 g of ferric chloride. Then acetyl chloride is added from a dropping funnel in the quantity of 14.6 g (0.186 mole, i.e. a 35 percent excess with respect to the stoichiometric quantity) at a rate that would ensure the rise of temperature in the reaction mixture to not higher than 40° C. As soon as the whole quantity has been added, the reaction mixture is heated to 60° – 70° C and kept at this temperature for two hours. After rectification on a column (ten theoretical plates) the yield of (para-pentafluoroethoxyphenyl)methyldichlorosilane is 36.9 g, or 96.5 percent of theory.

The boiling point is 85° C (at 6 mm Hg) $d_4^{20} = 1.3975$; $n_D^{20} = 1.4374$ Found: $MR_D = 60.93$, $C_9H_7SiOF_5Cl_2$ Calculated: $MR_D = 60.54$ Elemental analysis Found, in percent: Si, 8.2, 8.5; Cl, 21.90, 21.76; F, 29.30, 29.51 $C_9H_7SiOF_5Cl_2$ Calculated, in percent; Si, 8.61; Cl, 21.84; F, 29.23

EXAMPLE 6

Preparation of (para-pentafluoroethoxyphenyl)methyldichlorosilane from para-bromo(pentafluoroethoxy)benzene.

Para-bromo(pentafluoroethoxy)benzene is prepared by a procedure similar to that described in Example 5.

The end product— (para-pentafluoroethoxyphenyl)methyldichlorosilane is synthesized as follows.

A three-neck flask is charged with 4.34 g (0.17 g-atom + a 5 percent excess with respect to the stoichiometric quantity) of magnesium in 180 ml of absolute diethyl ether and then, at a temperature of 36° C (the boiling point of diethyl ether), five drops of para-bromo(pentafluoroethoxy)benzene are added, and finally two drops of methyl iodide are introduced. As soon as the solution becomes turbid, the temperature in the flask is lowered to 8° C and, at this temperature, a solution of para-bromo(pentafluoroethoxy)benzene in absolute diethyl ether is added with intensive stirring within four hours. The total quantity of para-bromo(pentafluoroethoxy)benzene in absolute diethyl ether added is 49.5 g (0.17 mole). The reaction mixture is then heated to 36° C and kept at this temperature for 30 minutes. The resultant product is para-magnesiumbromo(pentafluoroethoxy)benzene in absolute diethyl ether.

A three-neck flask is charged with 48.82 g (0.34 mole, i.e. a 100 percent excess with respect to the stoichiometric quantity) of methyltrichlorosilane in 200 ml of absolute hexane, and then, at a temperature of 18° – 20° C, a solution of para-magnesiumbromo(pentafluoroethoxy)benzene in diethyl ether is added from a dropping funnel. The temperature in the reaction zone rises to 30° C. As soon as the whole solution has been added, the reaction mixture is heated to 36° – 40° C and kept at this temperature for three hours with intensive stirring to complete the reaction. The solution is then filtered and the solvents (diethyl ether and hexane) are removed by distillation together with excess methyltrichlorosilane. The residue is rectified on a column (ten theoretical plates) to isolate 29.8 g (54 percent of theory) of (para-pentafluoroethoxyphenyl)methyldichlorosilane.

The boiling point is 85.1° C (at 6 mm Hg) $d_4^{20} = 1.397$; $n_D^{20} = 1.4372$ Found: $MR_D = 60.90$, $C_9H_7SiOF_5Cl_2$ Calculated; $MR_D = 60.54$ Elemental analysis Found, in percent: Si, 8.30, 8.45; Cl, 21.75, 21.85; F, 29.35, 29.41 $C_9H_7SiOF_5Cl_2$ Calculated, in percent: Si, 8.61; Cl, 21.84; F, 29.23.

EXAMPLE 7

Preparation of [meta-(perfluoro-1,4-dioxaamyl)phenyl]methyldichlorosilane from meta-bromo(perfluoro-1,4-dioxaamyl)-benzene.

First meta-bromo(perfluoro-1,4-dioxaamyl)benzene is prepared by the following procedure. A 70-ml stainless steel autoclave is charged with 6.7 g (0.02 mole) of meta-bromophenyl ester of difluoro(trifluoromethoxy)acetic acid, 8 g of hydrogen fluoride, and 4 g of sulphur tetrafluoride, and the contents are heated at a temperature of 100° C for two hours. When the reaction is complete the autoclave is cooled and gases are released out of it. The reaction products are distilled with steam, and the distillate is extracted with diethyl ether. The ethereal extract is washed with water, a 10 percent aqueous solution of sodium hydroxide, again with water, and dried over sodium sulphate. Diethyl ether is removed by distillation, and the residue is distilled in vacuum. The yield of meta-bromo(perfluoro-1,4-dioxaamyl)benzene is 5.46 g, i.e. 76.5 percent of theory. The boiling point is 82° – 85° C at 200 mm Hg. $d_4^{20} = 1.673$; $n_D^{20} = 1.4063$ Found: $MR_D = 52.48$. $C_9H_4O_2BrF_7$ Calculated: $MR_D = 52.69$ Elemental analysis Found, in percent: Br, 22.01, 22.30; F, 37.44, 37.62. $C_9H_4O_2BrF_7$ Calculated, in percent: Br, 22.41; F, 37.25

The end product — [meta-(perfluoro-1,4-dioxaamyl)phenyl]-methyldichlorosilane is synthesized as follows.

A three-neck flask is charged with 4.05 g (0.185 g-atom + a 10 percent excess with respect to the stoichiometric quantity) of magnesium in 200 ml of absolute tetrahydrofurane and then, at a temperature of 56° C (the boiling point of tetrahydrofurane), five drops of meta-bromo(perfluoro-1,4-dioxaamyl)benzene, having the formula

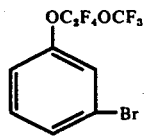

(III)

are added, and finally two drops of methyl iodide are introduced.

When the solution becomes turbid, the temperature in the flask is lowered to 8° C and, at this temperature, a solution of meta-bromo(perfluoro-1,4-dioxaamyl)benzene in absolute tetrahydrofurane is added with intensive stirring within six hours. The total quantity of meta-bromo(perfluoro-1,4-dioxaamyl)benzene added into the flask is 31.13 g (0.185 mole) in 70 ml of absolute tetrahydrofurane. The reaction mixture is then heated to 50° – 60° C and kept at this temperature for thirty minutes. The resultant product is meta-magnesiumbromo(perfluoro-1,4-dioxaamyl)benzene in absolute tetrahydrofurane.

A three-neck flask is charged wth 82.9 g (0.555 mole, i.e. a 200 percent excess with respect to the stoichiometric quantity) of methyltrichlorosilane in 300 ml of absolute hexane, and then, at a temperature of 18° – 20° C, meta-magnesiumbromo(perfluoro-1,4-dioxaamyl)benzene in tetrahydrofurane is added from a dropping funnel. The temperature in the reaction zone rises to 30° C. As soon as the whole quantity of the solution has been added, the temperature of the reaction mixture is raised to 56° – 60° C and the mixture is kept at this temperature for three hours with intensive stirring. The solution is then filtered and the solvents (tetrahydrofurane and hexane) are distilled off together with excess methyltrichlorosilane. The residue is rectified on a column (10 theoretical plates) to isolate 46.2 g (67.5 percent of theory) of [meta-(perfluoro-1,4-dioxaamyl)phenyl]methyldichlorosilane having the formula

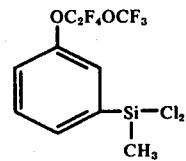

(IV)

The boiling point is 85.5° C and 5 mm Hg; $d_4^{20} = 1.452$; $n_D^{20} = 1.4160$ Found: $MR_D = 67.57$. $C_{10}H_7SiO_2F_7Cl_2$ Calculated: $MR_D = 67.0$ Elemental analysis Found, in percent: C, 30.60, 30.75; H, 1.8, 1.95; F, 33.72, 33.81; Si, 6.60, 6.82; Cl, 18.25, 18.40. $C_{10}H_7SiO_2F_7Cl_2$ Calculated, in percent: C, 30.69; H, 1.79; F, 34.01; Si, 7.16; Cl, 18.15

EXAMPLE 8

Preparation of [meta-(perfluoro-3-oxabutyl)phenyl]methyldichlorosilane from meta-bromo(perfluoro-3-oxabutyl)benzene.

First meta-bromo(perfluoro-3-oxabutyl)benzene is prepared as follows. 55 g (0.34 mole) of bromine are added to 150 g of (0.57 mole) of (perfluoro-3-oxabutyl)benzene, the solution is heated to 45° – 50° C and antimony pentachloride is added in 0.25 ml portions at ten-minute intervals with intensive stirring of the mixture. In an hour, the temperature of the solution is lowered to 30° – 31° C and further bromination is carried out at this temperature. As the solution becomes colourless, new portions of bromine (1 – 1.5 ml) are added with simultaneously determining the content of meta-bromo(perfluoro-3-oxabutyl)benzene in the solution. The total quantity of antimony pentachloride added is about 55 ml, and the total quantity of bromine, 91.2 g. The process is carried out within 33 – 37 hours. During this time the conversion of (perfluoro-3-oxabutyl)benzene is 87 – 92 percent. The process is then stopped and 500 ml of water containing 50 ml of saturated solution of potassium metabisulphite are added to bind the unreacted bromine. The reaction products are distilled with stream, neutralized with a 5 percent solution of sodium hydroxide, dried over calcium chloride, and rectified. The yield of meta-bromo(perfluoro-3-oxabutyl)benzene is 128.7 g (66 percent of theory).

The boiling point is 103° C (at 25 mm Hg) $d_4^{20} = 1.676$; $n_D^{20} = 1.4180$ Found: $MR_D = 51.27$. $C_9H_4F_7OBr$ Calculated: $MR_D = 50.62$ Elemental analysis Found, in percent: C, 31.60; H, 1.30; F, 38.9; Br, 22.80 $C_9H_4F_7OBr$ Calculated, in percent: C, 31.67; H, 1.18; F, 39.0; Br, 23.43

The end product — [meta-(perfluoro-3-oxabutyl)phenyl]methyldichloroethane is synthesized as follows.

A three-neck flask is charged with 24.3 g (0.907 g-atom + a 10 percent excess with respect to the stoichiometric quantity) of magnesium in 600 ml of absolute diethyl ether and, at a temperature of 36° C (the boiling point of the ether), five drops of meta-bromo(perfluoro-3-oxabutyl)benzene, having the formula

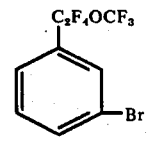

(V)

are added.

As the reaction begins (the solution becomes turbid the temperature in the flask is lowered to 10° C and metabromo(perfluoro-3-oxabutyl)benzene in absolute diethyl ether is added with intensive stirring of the reaction mixture within four hours. The total quantity of meta-bromo(perfluoro-3-oxabutyl)benzene added is 309 g (0.907 mole) in 300 ml of absolute diethyl ether. The reaction mixture is heated to 36° C and kept at this temperature for thirty minutes. The resultant product is a solution of meta-magnesium-bromo(perfluoro-3-oxabutyl)benzene in absolute diethyl ether.

A three-neck flask is charged with 229.5 g (1.36 mole, i.e. a 50 percent excess with respect to the stoichiometric quantity) of methylchlorodiethoxysilane in 600 ml of absolute hexane, and the solution of meta-magnesiumbromo(perfluoro-3-oxabutyl)benzene in absolute diethyl ether is added from a dropping funnel at a temperature of 18°–20° C. The temperature in the reaction mixture rises to 30° C, and as the whole said solution has been added, the reaction mixture is heated to 40° C and kept at thus temperature for three hours with intensive stirring. The solution is filtered, and the solvents (diethyl ether and hexane) are removed by distillation. The residue is rectified to obtain 310 g (86.8 percent of theory) of [meta-(perfluoro-3-oxabutyl)phenyl]methyldiethoxysilane.

The boiling point is 105.5° C (at 20 mm Hg) $d_4^{20}$ = 1.235; $n_D^{20}$ = 1.4006

Found: $MR_D$ = 77.39. $C_{14}H_{17}SiO_3F_7$ Calculated: $MR_D$ = 76.75 Elemental analysis Found, in percent: C, 42.45; H, 4,18; Si, 6.84; F, 33.62 $C_{14}H_{17}SiO_3F_7$ Calculated, in percent: C, 42.65; H, 4.27; Si, 7.10; F, 33.75

A three-neck flask is charged with 382 g (0.97 mole) of meta-(perfluoro-3-oxabutyl)phenyl methyldiethoxysilane and 0.05 g of ferric chloride, 228.4 g (2.91 mole, i.e. a 50percent excess with respect to the stoichiometric quantity) of acetyl chloride are added from a dropping funnel at a rate that would ensure the rise of temperature of the reaction mixture not above 40° C. As soon as the whole required quantity has been added, the reaction mixture is heated to 60°–70° C and kept at this temperature for two hours. After distillation of excess acetyl chloride, the residue is rectified on a column (ten theoretical plates) to isolate 316 g (90 percent of theory) of meta-(perfluoro-3-oxabutyl)phenyl methyldichlorosilane. The boiling point is 67.3° C (at 2 mm Hg) $d_4^{20}$ = 1.4340; $n_D^{20}$ = 1.4200

Found: $MR_D$ = 65.99. $C_{10}H_7SiOF_7Cl_2$ Calculated: $MR_D$ = 65.28 Elemental analysis Found, in percent; C, 32.05; H, 1.92; Si, 7.56; F, 35.24; Cl, 18.72 $C_{10}H_7SiOF_7Cl_2$ Calculated, in percent: C, 32.00; H, 1.86; Si, 7.46; F, 35.46; Cl, 18.93

EXAMPLE 9

Preparation of (meta-heptafluoropropylphenyl)methyldichlorosilane from meta-bromo(heptafluoropropyl)benzene.

First meta-bromo(heptafluoropropyl)benzene is prepared as follows. 12 g (0.04 mole) of antimony pentachloride are added to 389 g (1.58 mole) of heptafluoropropylbenzene and then, with intensive stirring, 41 ml (0.79 mole) of bromine are added in drops within an hour with simultaneously cooling the reaction mixture on a water bath. The temperature of the reaction mixture is maintained at 26° C maximum. After adding all the bromine, the reaction mixture is given another stirring for 15 minutes. In the course of the entire bromination reaction, dry chlorine is passed into the reaction mixture at a rate of 3 liters per hour. On completion of the reaction, for binding the unreacted bromine, the reaction mixture is poured into 500 ml of water containing 25 ml of saturated solution of sodium bisulphite. The reaction product is distilled with steam, neutralized with a 5 percent solution of sodium hydroxide dried over calcined calcium chloride, and rectified. The yield of meta-bromo(heptafluoropropyl)benzene is 447.2 g (87 percent of theory).

The boiling point is 174° C at 760 mm Hg $d_4^{20}$ = 1.670; $n_D^{20}$ = 1.4230

Found: $MR_D$ = 49.50 $C_9H_4BrF_7$ Calculated: $MR_D$ = 49.69 Elemental analysis Found, in percent: C, 33.15; H, 1.18; Br, 24.45. $C_9H_4BrF_7$ Calculated, in percent: C, 33.23; H, 1.23; Br, 24.64

The end product is synthesized as follows.

A three-neck flask is charged with 16.47 g (0.61 g-atom + a 10 percent excess with respect to the stoichiometric quantity) of magnesium in 300 ml of absolute diethyl ether, and then, at a temperature of 36° C (the boiling point of the ether), 5 drops of meta-bromo(heptafluoropropyl)benzene are added. Finally, four drops of methyl iodide are added to the solution and as soon as it becomes turbid, the temperature in the flask is lowered to 8° C and the solution of meta-bromo(heptafluoropropyl)benzene in absolute diethyl ether is added into the flask within four hours with intensive stirring of the reaction mixture. The total quantity of meta-bromo(heptafluoropropyl)benzene added is 200 g (0.61 mole) in 200 ml of absolute diethyl ether. The reaction mixture is then heated to 36° C and kept at this temperature for 40 minutes. The resultant product is meta-magnesiumbromo(heptafluoropropyl)benzene in absolute diethyl ether.

A three-neck flask is charged with 547.20 g (3.66 mole, i.e. a 500 percent excess with respect to the stoichiometric quantity) of methyltrichlorosilane in 300 ml of absolute hexane, and, at a temperature of 18° – 20° C, the solution of meta-magnesiumbromo(heptafluoropropyl)benzene in absolute diethyl ether is added from a dropping funnel. The temperature of the reaction mixture rises to 30° C. As soon as the whole required quantity is added, the reaction mixture is heated to 40° – 45° C and kept at this temperature for three hours with intensive stirring. The solution is then filtered, the solvents (diethyl ether and hexane) are removed together with excess methyltrichlorosilane. By distillation, the rectification gives 186.2 g of (meta-heptafluoropropylphenyl)methyldichlorosilane (85 percent of theory). The boiling point is 83° C (at 3 mm Hg) $d_4^{20}$ = 1.437; $n_D^{20}$ = 1.4283

Found: $MR_D$ = 64.20 Calculated: $MR_D$ = 64.43. $C_{10}H_7SiF_7Cl_2$ Elemental analysis Found, in percent: Cl, 19.65, 19.82; $C_{10}H_7SiF_7Cl_2$ Calculated, in percent: Cl, 19.80.

We claim:

1. [Perfluoroalkyl(alkoxy)phenyl]methyldichlorosilanes having the general formula

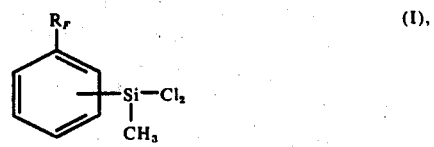

where: $R_F$ = $OCF_3$, $OC_2F_5$, $OC_2F_4OCF_3$, $C_2F_4OCF_3$, $C_3F_7$

2. A method of preparing [perfluoroalkyl(alkoxy)-phenyl]methyldichlorosilanes having the general formula

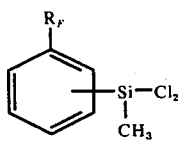
(I), where: $R_F$ = $OCF_3$, $OC_2F_5$, $OC_2F_4OCF_3$, $C_2F_4OCF_3$, $C_3F_7$ consisting in that fluorine-containing bromo[alkyl(alkoxy)]benzenes having the general formula

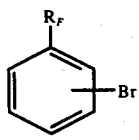
(II), where: $R_F$ = $OCF_3$, $OC_2F_5$, $OC_2F_4OCF_3$, $C_2F_4OCF_3$, $C_3F_7$ are treated with magnesium taken in a 5 – 20 percent excess with respect to the stoichiometric quantity, in a solution of a polar solvent, selected from the group consisting of absolute diethyl ether and absolute tetrahydrofurane, at a temperature of 8° – 60° C; the resulting fluorine-containing magnesium-bromo[alkyl(alkoxy)]benzenes are treated with a three-functional silane selected from the group consisting of methyltrichlorosilane and methylchlorodiethoxysilane, at a temperature of 18° – 60° C, said methyltrichlorosilane being taken in a 100 – 500 percent excess of the stoichiometric quantity, and said methylchlorodiethoxysilane being taken in a quantity ranging from the stoichiometric one to a 50 percent excess of the stoichiometric quantity; in case of methylchlorodiethoxysilanes, the resultant products being fluorine-containing [alkyl(alkoxy)phenyl]methyldiethoxysilanes are treated with acetyl chloride taken in a 25 – 50 percent excess with respect to the stoichiometric quantity, at a temperature of 40° – 70° C, in the presence of ferric chloride as a catalyst.

3. A method according to claim 2, in which fluorine-containing bromo[alkyl(alkoxy)]benzenes are treated with magnesium in the presence of methyl iodide.

4. A method according to claim 2, in which fluorine-containing magnesiumbromo[alkyl(alkoxy)]benzenes are treated with three-functional silanes in the presence of absolute hexane taken in the quantity of 30 – 400 percent of the weight of the three-functional silane.

* * * * *